US008374965B2

(12) United States Patent
Friend et al.

(10) Patent No.: US 8,374,965 B2
(45) Date of Patent: Feb. 12, 2013

(54) SYSTEM AND METHOD FOR VERIFYING THE CONTENTS OF A FILLED, CAPPED PHARMACEUTICAL PRESCRIPTION

(75) Inventors: Joshua Friend, Raleigh, NC (US); Christopher E. Paul, Hillsborough, NC (US); Stefano Bresolin, Durham, NC (US); Pete Klein, Durham, NC (US); Caelan Klein, legal representative, Williamsburg, MI (US); David Newcomb, Morrisville, NC (US)

(73) Assignee: Parata Systems, LLC, Durham, NC (US)

( * ) Notice: Subject to any disclaimer, the term of this patent is extended or adjusted under 35 U.S.C. 154(b) by 486 days.

(21) Appl. No.: 12/623,822

(22) Filed: Nov. 23, 2009

(65) Prior Publication Data

US 2010/0232640 A1 Sep. 16, 2010

Related U.S. Application Data

(60) Provisional application No. 61/118,011, filed on Nov. 26, 2008.

(51) Int. Cl.
*G06F 21/00* (2006.01)
*A61K 49/00* (2006.01)
(52) U.S. Cl. .......................... 705/50; 424/10.1
(58) Field of Classification Search .............. 705/75–76; 382/110, 207
See application file for complete search history.

(56) References Cited

U.S. PATENT DOCUMENTS

| 4,223,751 | A | 9/1980 | Ayers et al. |
| 4,695,163 | A | 9/1987 | Schachar |
| 5,337,902 | A | 8/1994 | Evans et al. |
| 5,337,919 | A | 8/1994 | Spaulding et al. |
| 5,504,332 | A | 4/1996 | Richmond et al. |
| 5,597,995 | A | 1/1997 | Williams et al. |
| 5,679,954 | A | 10/1997 | Soloman |
| 5,768,327 | A | 6/1998 | Pinto et al. |
| 5,826,696 | A | 10/1998 | Rupp et al. |
| 5,884,806 | A | 3/1999 | Boyer et al. |
| 5,907,493 | A | 5/1999 | Boyer et al. |
| 5,960,098 | A | 9/1999 | Tao |

(Continued)

FOREIGN PATENT DOCUMENTS

| EP | 0 452 905 A1 | 10/1991 |
| EP | 0 656 200 A2 | 6/1995 |

(Continued)

OTHER PUBLICATIONS

"Introduction to Spectroscopy", Michigan State University website, all pages. Retrieved May 10, 2012. http://www2.chemistry.msu.edu/faculty/reusch/VirtTxtJml/Spectrpy/spectro.htm.*

(Continued)

*Primary Examiner* — James A Reagan
*Assistant Examiner* — Calvin Cheung
(74) *Attorney, Agent, or Firm* — Myers Bigel Sibley & Sajovec

(57) ABSTRACT

A method of verifying the identity of a dispensed pharmaceutical includes the steps of: reading identifying indicia on a pharmaceutical vial containing a dispensed pharmaceutical; determining the identity of a prescribed pharmaceutical called for by the identifying indicia; acquiring an image of the dispensed pharmaceutical through the vial; comparing the image of the dispensed pharmaceutical to data storage comprising image data associated with pharmaceuticals; acquiring spectral data for the dispensed pharmaceutical through the vial; comparing the spectral data of the dispensed pharmaceutical to data storage comprising spectral data associated with pharmaceuticals; and automatically determining whether the image and the spectral data of the dispensed pharmaceutical confirm that the dispensed pharmaceutical matches the prescribed pharmaceutical.

23 Claims, 5 Drawing Sheets

U.S. PATENT DOCUMENTS

| | | |
|---|---|---|
| 6,310,686 B1 | 10/2001 | Jiang |
| 6,363,687 B1 | 4/2002 | Luciano et al. |
| 6,364,517 B1 | 4/2002 | Yuyama et al. |
| 6,373,567 B1 | 4/2002 | Wise et al. |
| 6,471,088 B1 | 10/2002 | Uema et al. |
| 6,497,342 B2 | 12/2002 | Zhang et al. |
| 6,509,537 B1 | 1/2003 | Krieg et al. |
| 6,522,945 B2 | 2/2003 | Sleep et al. |
| 6,535,637 B1 | 3/2003 | Wootton et al. |
| 6,607,094 B2 | 8/2003 | MacDonald |
| 6,690,464 B1 | 2/2004 | Lewis et al. |
| 6,771,369 B2 | 8/2004 | Rzasa et al. |
| 6,919,556 B1 | 7/2005 | Laurence |
| 7,006,214 B2 | 2/2006 | Rzasa et al. |
| 7,028,723 B1 | 4/2006 | Alouani et al. |
| 7,080,755 B2 | 7/2006 | Handfield et al. |
| 7,099,741 B2 | 8/2006 | Baranowski |
| 7,139,639 B2 | 11/2006 | Broussard et al. |
| 7,218,395 B2 | 5/2007 | Kaye et al. |
| 7,317,525 B2 * | 1/2008 | Rzasa et al. .......... 356/300 |
| RE40,453 E | 8/2008 | Lasher et al. |
| 2003/0176942 A1 | 9/2003 | Sleep et al. |
| 2004/0004085 A1 | 1/2004 | Williams et al. |
| 2004/0104241 A1 | 6/2004 | Broussard et al. |
| 2004/0133705 A1 | 7/2004 | Broussard et al. |
| 2004/0183237 A1 | 9/2004 | McGrath et al. |
| 2004/0207842 A1 | 10/2004 | Rzasa et al. |
| 2004/0263843 A1 | 12/2004 | Knopp et al. |
| 2005/0004495 A1 | 1/2005 | Goswami |
| 2005/0134856 A1 | 6/2005 | Rutledge |
| 2005/0248759 A1 | 11/2005 | Wang et al. |
| 2005/0288906 A1 | 12/2005 | Drennen, III et al. |
| 2006/0041330 A1 | 2/2006 | Ansari et al. |
| 2007/0008523 A1 | 1/2007 | Kaye et al. |
| 2007/0093932 A1 | 4/2007 | Abdulhay et al. |
| 2007/0150092 A1 | 6/2007 | Ohmura et al. |
| 2008/0061074 A1 | 3/2008 | Remis et al. |
| 2008/0183410 A1 | 7/2008 | Klein et al. |

FOREIGN PATENT DOCUMENTS

| | | |
|---|---|---|
| EP | 1 003 027 A1 | 5/2000 |
| WO | WO 97-48329 | 12/1997 |
| WO | WO 99/61324 | 12/1999 |
| WO | WO 02/069897 A2 | 9/2002 |
| WO | WO 2004/072868 A1 | 8/2004 |
| WO | WO 2005/031302 A2 | 4/2005 |
| WO | WO 2006-036434 | 4/2006 |

OTHER PUBLICATIONS

Strunk and White: The Elements of Style, 3$^{rd}$ Ed., MacMillan Publishing Co., p. 40, 1979.*
Aldridge et al., Identification of Tablet Formulations Inside Blister Packages by Near-Infrared Spectroscopy, 1994, vol. 48, No. 10, pp. 1272-1276, Applied Spectroscopy.
Alexander et al., New Technologies Forum 4: Process Measurement and Control, Date Unknown, pp. 1-18, Royal Pharmaceutical Society.
Analyst, Application of Near-Infrared Reflectance Spectrometry to the Analytical Control of Pharmaceuticals: ranitidine Hydrochloride tablet Production, Feb. 1996, vol. 121, pp. 219-222, Analyst.
Andrew Smith, What Really Counts is Separation, Sep. /Oct. 2002, pp. 82-88, Machinery Update.
Burns et al., NIR Analysis of Pharmaceuticals, 1992, vol. 13, pp. 549-563, Marcel Dekker, Inc., New York, New York, USA.
Choi et al., Spatially Resolved Broad-Band Dielectroscopy for Material Characterization, Jan. 30, 2001, pp. 1-11, Chemical & Fuels Engineering, University of Utah.
Chris Frank, Raman Analysis in Pharmaceuticals, Sep. 1998, pp. 1-4, Raman Review.
PCT International Search Report for PCT/US05/42342, 2005.
Dempster et al., Near-Infrared Methods for the Identification of Tablets in Clinical Trial Supplies, 1993, vol. 11, No. 11/12, pp. 1087-1092, Journal of Pharmaceutical & Biomedical Analysis.
Demptser et al., A Near-Infrared Reflectance Analysis Method for the Noninvasive Identification of Film-Coated and Non-Film Coated, Blister-Packed Tablets, 1995, pp. 43-51, Analytica Chimica Acta 310.
James K. Drennen and Robert A. Lodder, Nondestructive Near-Infrared Analysis of Intact Tablets for Determination of Degradation Products, Jul. 1990, vol. 79, No. 7, pp. 622-627, Journal of Pharmaceutical Sciences.
Journal of Pharmaceutical Sciences, Near-Infrared Spectroscopy and Imaging for the Monitoring of Powder Blend Homogeneity, Journal, Sep. 2001, vol. 90, No. 9, pp. 1298-1307, Journal of Pharmaceutical Sciences.
Kohn et al., Identification of Drugs by Near Infrared Spectra, 1992, vol. 37, No. 1, pp. 35-41, Journal of Forensic Sciences.
Lodder et al., Detection of Capsule Tampering by Near-Infrared Reflectance Analysis, Aug. 1, 1987, pp. 1921-1930, vol. 59, No. 15, American Chemical Society.
MacDonald et al., Some Applications of Near-Infrared Reflectance Analysis in the Pharmaceutical Industry, 1993, vol. 11, No. 11/12, pp. 1077-1085, Journal of Pharmaceutical & Biomedical Analysis.
Medical News Today, US Patent issued for Unique Prescription Verification Solution, Aug. 13, 2004, p. 1 of 1, Medical News Today.
Morisseau et al., Pharmaceutical Uses of Near-Infrared Spectroscopy, 1995, pp. 1071-1090, Drug Development and Industrial Pharmacy.
Nova Packaging Systems, New SV2 Intellisense, Retrieved Nov. 17, 2004 from Internet Site http://pei2004.packexpo.com/pei20004/packaging_supp;iers/ve/37054/pr_63.html , p. 1 of 1, Nova Packaging Systems.
P.A. Hailey, The Role of NIR Spectroscopy in the Measurement of Pharmaceutical Manufacture, Retrieved Oct. 27, 2005 from Internet Site http://www.brimrose.com/hailey.html, pp. 1-6, Brimrose.
Packaging Digest, Diverse Filling Line is Flexible and Fast, Retrieved Oct. 16, 2011 from Internet Site http://www.packagingdigest.com/article/print/341813-Diverse_filling_line_is_flexible_and_fast.php Packaging Digest.
Packworld.com, Automated Tablet Packing, New Line Helps repackaging pay Off, Retrieved Oct. 25, 2005 from Internet Site http://www.packworld.com/cds_print.html?rec_id=12789, pp. 1-4, packworld.com.
Packworld.com, Electrostatic Sensing, retrieved Oct. 25,2005 from Internet Site http://www.packworld.com/cds_print.html?rec_id=12621 p. 1 of 1, Packworld.com.
Parmeter et al., Guide for the Selection of Drug Detectors for Law Enforcement Applications NIJ guide 601-00, Aug. 2000, 64 pages, National Institute of Justice.
Pat Reynolds, Electrostaticosensing, Retrieved Nov. 17, 2004 from Internet Site http://www.dtindustries.com/packaging/packworldstory.asp_page_1_of_1, DT Packaging Systems industries.
Pharmaceutical Analytical Sciences Group, Guidelines for the Development and Validation of Near Infrared (NIR) Spectroscopic Methods, Oct. 2001, pp. 1-41, Pharmaceutical Analytical Sciences Group.
Polli et al., Technology Vs Fake Drgs, retrieved Oct. 27, 2005 from Internet Site http://www.uspharmacist.com/index.asp?show=article&page=8_120.htm pp. 1-2, U.S. Pharmacist.
Presearch Limited, Technical Note N-DT-01 Statistical Analysis, Oct. 2002, pp. 1-5, Presearch Limited.
Spectrolab Life Sciences, DASI—A Unique Hand Carried Analyser for Drug Identification & Molecular Analysis, Date Unknown, p. 1 of 1, Spectrolab Life Sciences, Internet Site www.spectrolab.co.uk.
Supplemental European Search Report for EP 05 82 5091 dated Aug. 27, 2010.
Tony Lam, A New Era in Affordable Raman Spectroscopy, Jun. 2004, pp. 30-36, Raman Technology for Today's Spectroscopists.
Wu et al., Spectral Transformation and Wavelength Selection in near-Infrared Spectra Classification, 1995, pp. 243-255, Analytica Chimica Acta 315.
International Search Report, mailed Jun. 25, 2008, for corresponding application PCT-US2008-000387.

International Search Report, mailed Dec. 7, 2009, for corresponding application PCT-US2009-057383.

* cited by examiner

SYSTEM AND METHOD FOR VERIFYING THE CONTENTS OF A FILLED, CAPPED PHARMACEUTICAL PRESCRIPTION

RELATED APPLICATION

This application claims priority from U.S. Provisional Patent Application No. 61/118,011, filed Nov. 26, 2008, the disclosure of which is hereby incorporated herein in its entirety.

FIELD OF THE INVENTION

The present invention is directed generally to the identification of pharmaceuticals, and more particularly to the automatic identification of dispensed pharmaceuticals.

BACKGROUND OF THE INVENTION

There is an ongoing and predicted long-term shortage of licensed pharmacists. Due to the increasing age of the population and the ever-increasing number of prescription medicines available, the demand for prescription drugs is growing at a rate that will far exceed the capacity and numbers of licensed pharmacists. The net impact of this imbalance is that pharmacists are increasingly spending more time doing clerical and administrative tasks such as verifying filled prescriptions and checking data entry done by pharmacy technicians. Since the capacity of any one pharmacist is fixed, the output of a pharmacy has become constrained. Consequently, the labor and total cost per prescription continues to rise. The December 2000 Department of Health and Human Services Report to Congress titled "The Pharmacist Workforce: A Study of the Supply and Demand for Pharmacists", which is hereby incorporated herein by reference, provides an overview of the above problem.

Due to these increased demands on a pharmacist's time, and the resulting increased reliance on technicians and other non-professional staff to fill prescriptions, there is an increased chance for prescription error. While these errors may take many font's, the likelihood of a dangerous or life threatening "adverse drug event" increases proportionally with the increased chance of prescription fill error. Several studies have shown that prescription error rates are consistently in the 2% to 7% range, with a 4% error rate often cited as a reliable average. The number of deaths due to medication errors is estimated to exceed 7,000 per year in the United States alone. Of course, this number does not include nonfatal conditions from drugs that also result in some form of trauma or injury. The resulting litigation costs associated with these prescription fill errors have also dramatically increased.

Many existing pharmacy filling systems and procedures still require a human operator, whether that operator is a technician or a licensed pharmacist, to validate visually whether the drug that is delivered to the customer is correct. Thus, the human factor can contribute to the majority of prescription fill errors. Existing visual verification techniques rely on comparing an electronic image of the prescribed medication, i.e., a picture of the prescribed medication retrieved from a data library, with the actual medication that is dispensed for the patient. Other systems and procedures rely on comparing the dispensed medication with that in the original manufacturer's supply container, or comparing an electronic image of the filled prescription with an electronic image of the prescribed medication retrieved from a data library.

Each of these verification systems present similar problems. First, these known verification methods assume that all drugs are visually distinct. This assumption causes many problems because many drugs are not, in fact, visually distinct and, in other cases, the visual differences between drugs is very subtle. For instance, manufacturers are rapidly running out of unique shapes, colors and sizes for their solid dosage form products. To further complicate the problem, generic drug manufacturers may be using shapes, colors, and sizes that are different than that of the original manufacturer. Second, even though some known systems may utilize a National Drug Code (NDC) bar code to verify that the supply bottle being accessed corresponds correctly to the patient's prescription, a fraction of filled prescriptions are never picked up and may be returned to the supply shelves for reuse in later prescriptions. These reused bottles will not, therefore, have a manufacturer's bar code on them. It is, therefore, difficult, if not impossible, to incorporate such validation schemes for these unused prescriptions. Furthermore, in these circumstances, a supply bottle is not available for a visual comparison with the filled prescription. Finally, each of these known manual verification and validation techniques typically requires that the pharmacist spend a significant portion of his day performing these administrative or clerical tasks and allows less time for patient consultation and other professional pharmacist activities.

Solid dosage pharmaceuticals (e.g., pills, tablets, and capsules) each have a unique chemical composition associated with them. This is often referred to as a chemical signature or fingerprint. Pharmaceuticals with varying dosage levels of the same active ingredient may have unique chemical signatures as well. Even slight variations in the active ingredient typically produce a unique chemical signature. In that regard, most pharmaceuticals can be identified accurately by the use of some form of chemical analysis. This same methodology may be applied to other forms of medication (e.g., liquids, creams, and powders). Particularly with solid dosage pharmaceutical products, while a group or package of products may look identical in the visible portion of the spectrum each product may have a unique chemical signature in the near-infrared wavelength range (800 to 2500 nm). For example, U.S. Pat. No. 6,771,369 to Rzasa et al. describes a pharmaceutical discrimination system that relies on near infrared (NIR) radiation for scanning the contents of a pharmaceutical vial. As another example, U.S. Pat. No. 7,218,395 to Kaye et al. describes the use of Raman spectroscopy for scanning vial contents. As a further example, co-assigned and co-pending U.S. patent application Ser. No. 11/972,849, filed Jan. 11, 2008, discusses a system that scans through the bottom end of the vial as the vial is capped. The disclosures of these patents and applications are hereby incorporated herein in their entireties.

It may be desirable to enhance the reliability and precision of systems that employ spectroscopic verification of pharmaceuticals within vials. As such systems become substantially more robust and complex, operating software that is correspondingly robust is needed to facilitate user interaction and control of these machines.

SUMMARY OF THE INVENTION

As a first aspect, embodiments of the present invention are directed to a method of verifying the identity of a dispensed pharmaceutical. The method includes the steps of: reading identifying indicia on a pharmaceutical vial containing a dispensed pharmaceutical; determining the identity of a prescribed pharmaceutical called for by the identifying indicia;

acquiring an image of the dispensed pharmaceutical through the vial; comparing the image of the dispensed pharmaceutical to data storage comprising image data associated with pharmaceuticals; acquiring spectral data for the dispensed pharmaceutical through the vial; comparing the spectral data of the dispensed pharmaceutical to data storage comprising spectral data associated with pharmaceuticals; and automatically determining whether the image and the spectral data of the dispensed pharmaceutical confirm that the dispensed pharmaceutical matches the prescribed pharmaceutical.

As a second aspect, embodiments of the present invention are directed to a system for verification of dispensed pharmaceuticals. The system includes: an identification station configured to read identifying indicia on a pharmaceutical vial containing a dispensed pharmaceutical; an image station configured to acquire an image of the dispensed pharmaceutical through the vial; a spectroscopy station configured to acquire spectral data for the dispensed pharmaceutical through the vial; and a controller associated with the identification, vision, and spectroscopy stations. The controller is configured to: receive the identifying indicia from the identification station; automatically determine the identity of a prescribed pharmaceutical called for by the identifying indicia; receive the image of the dispensed pharmaceutical from the image station; compare the image of the dispensed pharmaceutical to data storage comprising image data associated with pharmaceuticals; receive the spectral data of the dispensed pharmaceutical from the spectroscopy station; compare the spectral data of the dispensed pharmaceutical to data storage comprising spectral data associated with pharmaceuticals; and automatically determine whether the image and the spectral data of the dispensed pharmaceutical confirm that the dispensed pharmaceutical matches the prescribed pharmaceutical.

Although described above primarily with respect to system and method aspects of the present invention, it will be understood that the present invention may also be embodied as computer program products.

DETAILED DESCRIPTION OF EMBODIMENTS OF THE INVENTION

Figure 1:
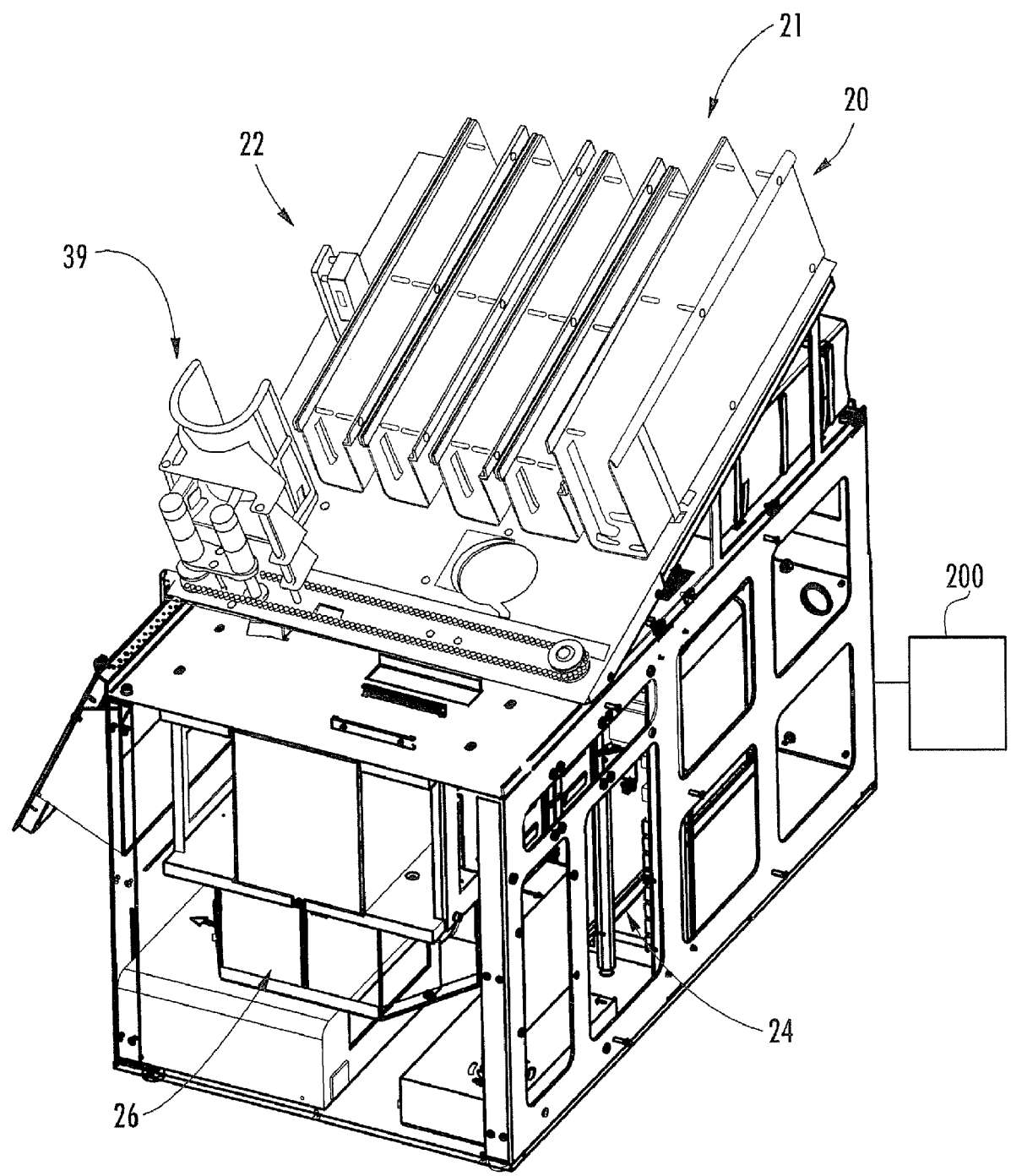
FIG. 1 is a front, right perspective view of a pharmaceutical verification system according to embodiments of the present invention.

The present invention now will be described more fully hereinafter with reference to the accompanying drawings, in which illustrated embodiments of the invention are shown. This invention may, however, be embodied in many different fauns and should not be construed as limited to the embodiments set forth herein. Rather, these embodiments are provided so that this disclosure will be thorough and complete, and will fully convey the scope of the invention to those skilled in the art. Like numbers refer to like elements throughout.

As used herein, the singular forms "a," "an," and "the" are intended to include the plural fauns as well, unless expressly stated otherwise. It will be further understood that the terms "includes," "comprises," "including," and/or "comprising," when used in this specification, specify the presence of stated features, steps, operations, elements, and/or components, but do not preclude the presence or addition of one or more other features, steps, operations, elements, components, and/or groups thereof. It will be understood that when an element is referred to as being "connected" or "coupled" to another element, it can be directly connected or coupled to the other element or intervening elements may be present. Furthermore, "connected" or "coupled" as used herein may include wirelessly connected or coupled. As used herein, the term "and/or" includes any and all combinations of one or more of the associated listed items.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly faunal sense unless expressly so defined herein.

The present invention may be embodied as systems, methods, and/or computer program products for carrying out various operations of an automated pharmaceutical verification system. Accordingly, the present invention may be embodied in hardware and/or in software (including firmware, resident software, micro-code, etc.). Furthermore, the present invention may take the form of a computer program product on a computer-usable or computer-readable storage medium having computer-usable or computer-readable program code embodied in the medium for use by or in connection with an instruction execution system. In the context of this document, a computer-usable or computer-readable medium may be any medium that can contain, store, communicate, propagate, or transport the program for use by or in connection with the instruction execution system, apparatus, or device.

The computer-usable or computer-readable medium may be, for example, but not limited to, an electronic, magnetic, optical, electromagnetic, infrared, or semiconductor system, apparatus, or device. More specific examples (a non-exhaustive list) of the computer-readable medium would include the following: an electrical connection having one or more wires, a portable computer diskette, a random access memory (RAM), a read-only memory (ROM), an erasable programmable read-only memory (EPROM or Flash memory), and a portable compact disc read-only memory (CD-ROM).

The present invention is described herein with reference to flowchart illustrations and block diagram illustrations of methods, systems, and computer program products for implementing the various operations of an automated pharmacy machine, according to embodiments of the present invention. It will be understood that each block of the flowchart and/or block diagram illustrations, and combinations of blocks in the flowchart and/or block diagram illustrations, may be implemented by computer program instructions and/or hardware operations. These computer program instructions are provided to a processor, or other programmable data processing apparatus to produce a machine, such that the instructions execute via the processor and create means for implementing the functions specified in the flowcharts and block diagram blocks.

These computer program instructions may also be stored in a computer usable or computer-readable memory such that the instructions produce an article of manufacture including instructions that implement the functions specified in the flowcharts and block diagram blocks.

It should also be noted that in some alternate implementations, the functions/acts noted in the blocks may occur out of the order noted in the flowcharts. For example, two blocks shown in succession may in fact be executed substantially concurrently or the blocks may sometimes be executed in the reverse order, depending upon the functionality/acts involved. Moreover, the functionality of a given block of the flowcharts and/or block diagrams may be separated into multiple blocks and/or the functionality of two or more blocks of the flowcharts and/or block diagrams may be at least partially integrated.

The computer program instructions may also be loaded onto a controller or other programmable data processing apparatus to cause a series of operational steps to be performed on the controller or other programmable apparatus to produce a computer implemented process such that the instructions that execute on the controller or other programmable apparatus provide steps for implementing the functions specified in the flowcharts and block diagram blocks.

Computer program code for carrying out operations may be written in a high-level programming language, such as Python, Java, C, and/or C++, for development convenience. In addition, computer program code for carrying out operations of embodiments of the present invention may also be written in other programming languages, such as, but not limited to, interpreted languages. Some modules or routines may be written in assembly language or even micro-code to enhance performance and/or memory usage. It will be further appreciated that the functionality of any or all of the program modules may also be implemented using discrete hardware components, one or more application specific integrated circuits (ASICs), or a programmed digital signal processor or microcontroller. Embodiments of the present invention are not limited to a particular programming language.

Figure 2:
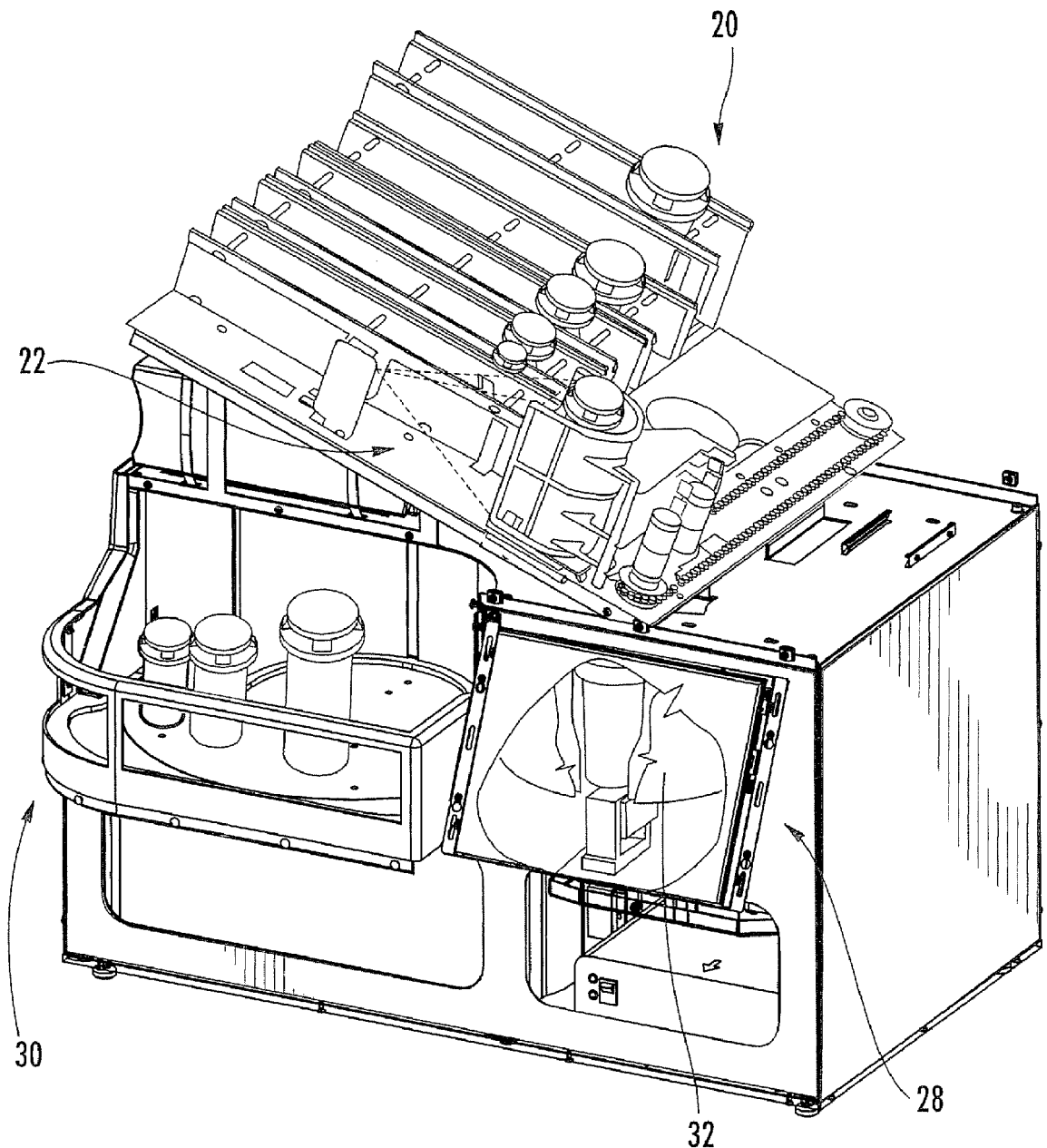
FIG. 2 is a front, left perspective view of a pharmaceutical verification system of FIG. 1.

Turning now to the figures, FIGS. 1 and 2 illustrate a pharmaceutical verification system 20 according to embodiments of the present invention. The system 20 includes a vial loading station 21, an identification, bar code scanning or RFID reading station 22, a vision station 24, a spectroscopy station 26, a stamping station 28, and an offload station 30. Vials are moved between these stations with a sliding conveyor 39 and a wheel conveyor 32. A controller 200 controls the operation of the various stations, the sliding conveyor 39 and the wheel conveyor 32. The operation of the system 20 is described in greater detail in co-pending and co-assigned U.S. Provisional Patent Application Ser. No. 61/118,006, entitled System and Method for Verifying the Contents of a Filled, Capped Pharmaceutical Prescription, filed Nov. 26, 2008 and U.S. patent application Ser. No. 12/623,917, filed concurrently and entitled System and Method for Verifying the Contents of a Filled, Capped Pharmaceutical Prescription, the disclosure of each of which is hereby incorporated herein in its entirety.

Figure 3:
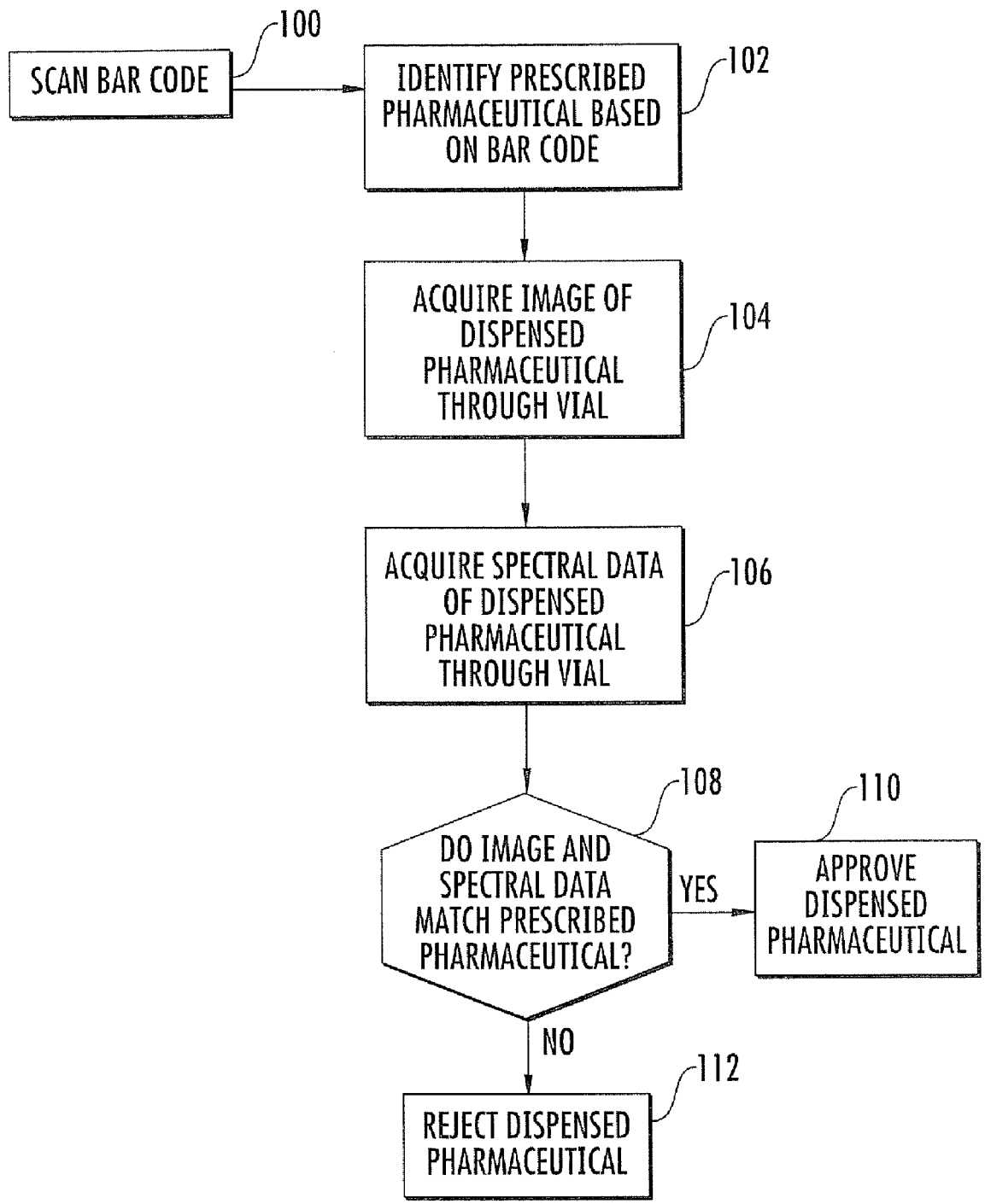
FIG. 3 is a flow chart depicting operations according to embodiments of the present invention.

The system 20, controlled by the controller 200, can perform operations as set forth in FIG. 3. The system 20 first reads identifying indicia on a pharmaceutical vial or package containing a dispensed pharmaceutical. In the illustrated embodiment, the system 20 first scans a bar code on the label of a pharmaceutical vial filled with a pharmaceutical (Block 100). In the bar code scanning station 22, the system 20 identifies from the bar code the pharmaceutical prescribed for the vial (the "prescribed pharmaceutical") (Block 102). In some embodiments, the system 20 identifies from the bar code various additional information, such as quantity of prescribed pharmaceutical dispensed, the size or shape of the vial to be used, or the like. In some embodiments, the controller 200 correlates the bar code with a particular NDC. This may be accomplished, for example, via an interface with a pharmacy software system. Those skilled in this art will appreciate that other techniques of reading information about the prescribed pharmaceutical from a vial, such as RFID, may also be employed.

The system 20 then acquires an image of the pharmaceutical in the vial (the "dispensed pharmaceutical") in the vision station 24 (Block 104). In the spectroscopy station 26, the system 20 next acquires spectral data of the dispensed pharmaceutical through the vial (Block 106). The controller 200 then determines whether the identity of the dispensed pharmaceutical identified with the image and spectral data matches (e.g., uniquely matches) the identity of the prescribed pharmaceutical (Diamond 108). If there is a match, the system 20 then approves the dispensed pharmaceutical in the stamping station 28 (Block 110), which in the illustrated embodiment comprises stamping the vial with a stamp of approval. If the identities of the dispensed pharmaceutical and the prescribed pharmaceutical do not match, the dispensed pharmaceutical is rejected (Block 112).

Figure 4:
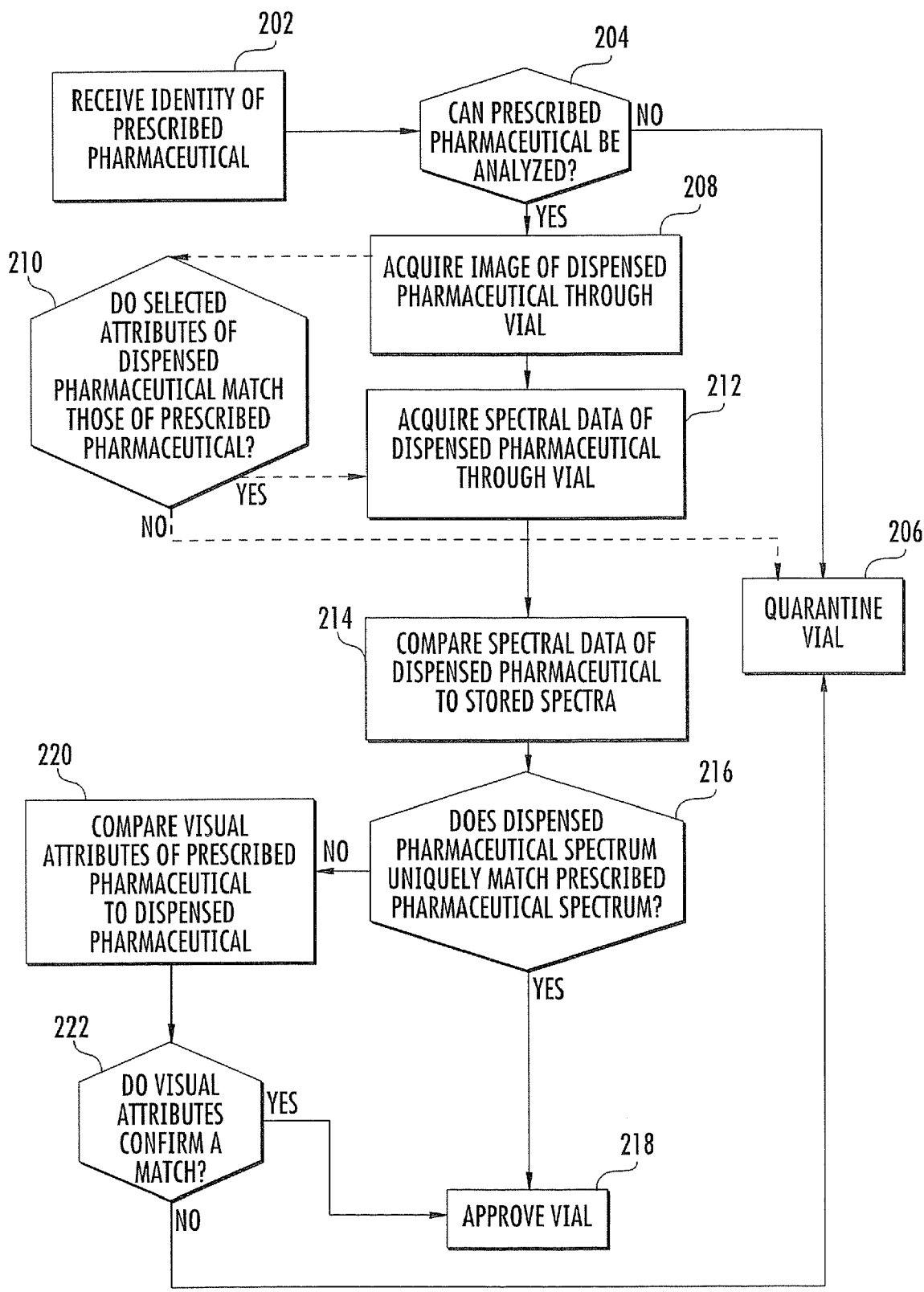
FIG. 4 is a flow chart depicting operations according to embodiments of the present invention.

Turning now to FIG. 4, a more detailed chart of the imaging and spectroscopy operations is illustrated. Initially, the controller 200 receives the identity of the prescribed pharmaceutical from the bar code scanning station 22 (Block 202). The controller 200 then compares the identity of the prescribed pharmaceutical to a data storage system, such as a database that indicates whether or not the prescribed pharmaceutical is one that can be positively distinguished by image and spectroscopic analysis (Diamond 204). If the prescribed pharmaceutical cannot be distinguished by image and spectral analysis (for example, Captopril 25 mg NDC 143117210, because the color, size, shape and spectral characteristics are similar to Captopril 12.5 mg NDC 143117110), the vial or package is rejected and quarantined (Block 206). In some embodiments, if the prescribed pharmaceutical cannot be distinguished by image and spectroscopic analysis, an image and/or spectral data of the dispensed pharmaceutical may nonetheless be acquired and stored for future access, as described in more detail below, prior to the vial being quarantined. A quarantined vial can subsequently be examined manually for verification. In some embodiments, if the bar code is not able to be scanned for any reason, or if information cannot be read from the bar code, the vial may be quarantined (Block 206). In some embodiments, if the information about the dispensed pharmaceutical that is obtained upon scanning of the bar code indicates that spectral or image data cannot be obtained (for example, if the quantity is too low for the system 20 to accurately collect data), the vial may be quarantined (Block 206).

If the prescribed pharmaceutical is one that can be distinguished by image and spectral analysis, the controller 200 directs the system 20 to acquire an image of the dispensed pharmaceutical through the vial (Block 208). In some embodiments, the controller 200 directs the system 20 to acquire an image of the dispensed pharmaceutical in the vial (i.e., the image need not be acquired "through" the vial). In the image acquisition step, the image can be taken with any digital camera known to be suitable for this purpose. An exemplary camera is Model Lw570c, available from Lumenera Corporation, Ottawa, Canada. Details of a suitable arrangement and operation are described in U.S. patent application Ser. No. 12/249,402, filed Oct. 10, 2008, U.S. Provisional Patent Application Ser. No. 61/118,014, entitled Assembly, System and Method for Acquiring Images, filed Nov. 26, 2008, and U.S. patent application Ser. No. 12/623,878, filed concurrently and entitled System and Method for Acquiring Images, the disclosure of each of which is hereby incorporated herein in its entirety.

As an optional step, the controller 200 may compare one or more selected visual attributes of the dispensed pharmaceutical (such as color, shape, size, text markings, scoring, or the like) to data stored for the prescribed pharmaceutical (Diamond 210). In some embodiments, this step will comprise selecting one or more visual attributes for the prescribed pharmaceutical that are particularly visually distinctive. For example, Zocor, available from Merck & Co., Whitehouse Station, N.J., has a distinctive shape that distinguishes it from other pharmaceuticals. Other pharmaceuticals may rely on color, size, markings on the pills, or the like as particularly distinctive visual attributes. In some embodiments, this step will comprise determining (e.g., automatically determining) whether the image of the dispensed pharmaceutical and the one or more visual attributes of the prescribed pharmaceutical confirm that the dispensed pharmaceutical uniquely matches the prescribed pharmaceutical.

In the comparison of the acquired image of the dispensed pharmaceutical to that of the prescribed pharmaceutical, known techniques for comparing images can be employed. The image(s) may be compared directly, or data derived from the processing of the image(s) may be compared. An exemplary visual comparison technique would involve using grayscale values to identify regions of interest wherein average color values are used as discriminating parameters. Exemplary techniques are also described in U.S. Pat. No. 6,535,637 to Wootton et al., the disclosure of which is hereby incorporated herein in its entirety.

In embodiments in which the initial image comparison is made, if the selected visual attributes of the dispensed pharmaceutical do not match those of the prescribed pharmaceutical, the vial is quarantined and rejected (Block 206) (in some embodiments, spectral data may be collected anyway for archiving purposes prior to the vial being quarantined). If the visual attributes of the dispensed pharmaceutical match those of the prescribed pharmaceutical, the controller 200 directs the system 20 to acquire spectral data of the dispensed pharmaceutical (Block 212). Spectral data can be acquired by any technique and/or with any apparatus known to those of skill in this art. An exemplary technique and system are described in U.S. patent application Ser. No. 11/972,849, supra.

The controller 200 next compares the spectral data of the dispensed pharmaceutical to spectral data for the prescribed pharmaceutical (Block 214). In comparing the spectrum of the dispensed pharmaceutical with that of the prescribed pharmaceutical, various techniques can be employed. Exemplary techniques for comparing and matching spectral data are discussed in U.S. Pat. No. 6,771,369 to Rzasa et al., U.S. Pat. No. 7,218,395 to Kaye et al., and U.S. patent application Ser. No. 11/972,849, supra, and may include absolute value and first and second derivative least-squares techniques.

Based on the comparison of spectral data, the controller 200 determines whether the spectral data of the dispensed pharmaceutical uniquely match the stored spectral data for the prescribed pharmaceutical (Diamond 216). In conducting this inquiry, the system 20 is providing a check to ensure that the dispensed pharmaceutical is indeed the prescribed pharmaceutical. Most image and spectral comparison techniques involve the production of a score, or rating, that determines the level of matching between the acquired data and the stored data. Anything above a certain score (e.g., a 95 percent similarity) is considered to be a match. However, such determinations do not preclude the possibility of more than one pharmaceutical providing similar spectral and image data. Thus, the inquiry determines whether any other possible spectral matches exist. The vial can be approved (Block 218) if no other possible spectral matches exist, and the system 20 can proceed to process another vial.

If, in Diamond 216, other spectral matches are possible, the controller 200 compares visual attributes of the prescribed pharmaceutical to the image of the dispensed pharmaceutical (Block 220). If optional step 210 was performed, such that at least one visual attribute has already been compared, then the controller 200 will compare other visual attributes in step 220 (e.g., if color was compared in step 210, then perhaps shape may be compared here). These operations can be conducted in the same manner as described above in connection with steps 208 and 210. The controller 200 then determines whether the additional visual attributes can confirm that the dispensed pharmaceutical cannot be anything other than the prescribed pharmaceutical (Diamond 222). In some embodiments, this step will comprise determining (e.g., automatically determining) whether the image of the dispensed pharmaceutical and the selected visual attribute(s) of the prescribed pharmaceutical confirm that the dispensed pharmaceutical uniquely matches the prescribed pharmaceutical. If a match is confirmed, the vial is approved (Block 218); if not, the vial is quarantined (Block 206).

Figure 5:
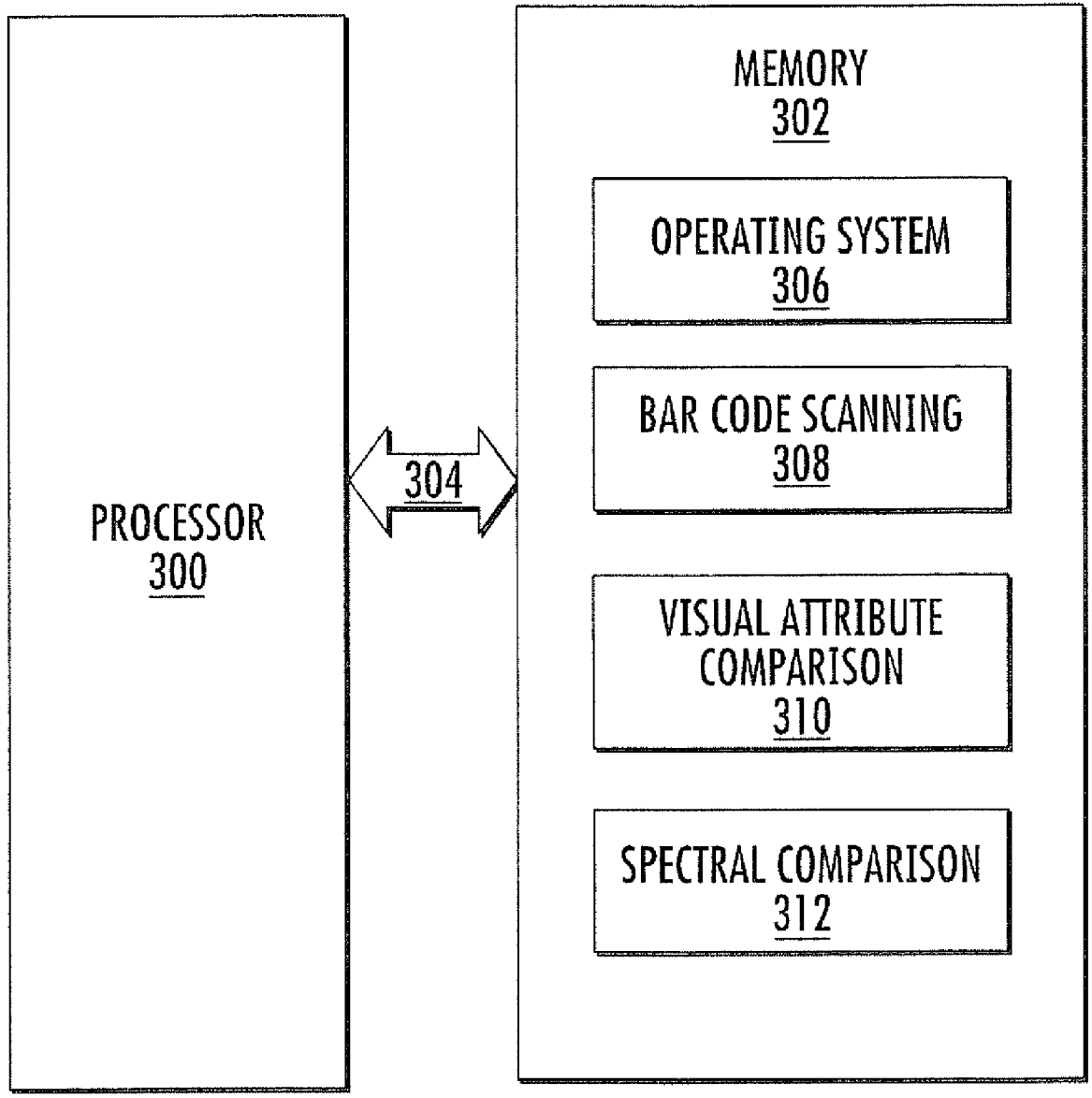
FIG. 5 is a block diagram of system architecture for implementing operations according to embodiments of the present invention.

FIG. 5 illustrates an exemplary processor 300 and memory 302 that may be utilized to implement the controller 200 of FIG. 1, according to some embodiments. The processor 300 communicates with the memory 302 via an address/data bus 304. The processor 300 may be, for example, a commercially available or custom microprocessor. The memory 302 is representative of the overall hierarchy of memory devices containing the software and data used to implement a device or system for creating and managing secure passwords as described herein, in accordance with some embodiments. The memory 302 may include, but is not limited to, the following types of devices: hard disk, solid state drive, cache, ROM, PROM, EPROM, EEPROM, flash, SRAM, and DRAM.

As shown in FIG. 5, the memory 302 may hold various categories of software and data: an operating system 306, a bar code scanning module 308, a visual attribute comparison module 310, and a spectral comparison module 312. The operating system 306 controls operations of the pharmaceutical verification system 20. In particular, the operating system 306 may manage the resources of the pharmaceutical verification system 20 and may coordinate execution of various programs (e.g., the bar code scanning module 308, visual attribute comparison module 310, the spectral comparison module 312, etc.) by the processor 300.

The bar code scanning module 308 comprises logic for scanning a bar code on the label of a pharmaceutical vial and for identifying from the bar code the pharmaceutical prescribed for the vial, as described above. The visual attribute comparison module 310 comprises logic for comparing one or more visual attributes of a dispensed pharmaceutical with data stored for a prescribed pharmaceutical, as described above. The spectral comparison module 312 comprises logic for comparing spectral data of a dispensed pharmaceutical with stored spectral data for the prescribed pharmaceutical, as described above.

In some embodiments, some or all of the data collected together with a history of the actions taken may be stored for future access. The system 20 may provide reporting about vials that fail validation, such as identifying the technician that dispensed it, and may also provide statistical information if a particular group of drugs is consistently affected by dispensing errors, which might help the pharmacy improve its workflow. Also, the images and spectral data that have been collected can be used as an evidence of the drug that was dispensed in case of a subsequent dispute regarding a prescription.

In addition, the a priori set of data may comprise information centrally collected by an organization that operates multiple systems 20. Such data may be deployed to the machines in the field. Because only small variations in the detection and operation from one system to another are to be expected, the data may be collected and processed in a way to ensure consistency of behavior across the fleet of systems; in other words, a system may not require training to build an a priori set of information collected by its own sensors.

Moreover, an organization may be able to update a fleet of systems. If a pharmacy tries to validate a drug with a drug code for which no data exists in the system, the validation for the drug fails. The system may be configured to signal a central information center of the drug for which validation was attempted. The central information center can then initiate an information collection process regarding that drug and remotely update systems in the field so that they can process the new drug.

The foregoing is illustrative of the present invention and is not to be construed as limiting thereof. Although exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention. The following claims are provided to ensure that the present application meets all statutory requirements as a priority application in all jurisdictions and shall not be construed as setting forth the scope of the invention.

That which is claimed is:

1. A method of verifying the identity of a dispensed pharmaceutical, comprising:
    reading identifying indicia on a pharmaceutical vial containing a dispensed pharmaceutical;
    determining the identity of a prescribed pharmaceutical called for by the identifying indicia;
    comparing the identity of the prescribed pharmaceutical to data storage comprising data that indicates whether the prescribed pharmaceutical is one that can be positively distinguished by image and spectral analysis; and
    responsive to the comparison of the identity of the prescribed pharmaceutical to data storage, either (a) rejecting the dispensed pharmaceutical when the comparison indicates that the prescribed pharmaceutical cannot be positively distinguished by image and spectral analysis, or (b) performing the following when the comparison indicates that the prescribed pharmaceutical can be positively distinguished by image and spectral analysis:
        acquiring an image of the dispensed pharmaceutical through the vial;
        comparing the image of the dispensed pharmaceutical to data storage comprising image data associated with pharmaceuticals;
        acquiring spectral data for the dispensed pharmaceutical through the vial;
        comparing the spectral data of the dispensed pharmaceutical to data storage comprising spectral data associated with pharmaceuticals; and
        automatically determining whether the image and the spectral data of the dispensed pharmaceutical confirm that the dispensed pharmaceutical matches the prescribed pharmaceutical.

2. The method of claim 1, further comprising approving the dispensed pharmaceutical responsive to a determination that the image and the spectral data of the dispensed pharmaceutical confirm that the dispensed pharmaceutical matches the prescribed pharmaceutical.

3. The method of claim 2, wherein approving the dispensed pharmaceutical comprises stamping the vial with a stamp of approval.

4. The method of claim 2, further comprising:
    collecting data associated with the approval of the dispensed pharmaceutical; and
    storing the data associated with the approval of the dispensed pharmaceutical in data storage for future access.

5. The method of claim 1, further comprising rejecting the dispensed pharmaceutical responsive to a determination that the image and the spectral data of the dispensed pharmaceutical do not confirm that the dispensed pharmaceutical matches the prescribed pharmaceutical.

6. The method of claim 5, wherein rejecting the dispensed pharmaceutical comprises quarantining the pharmaceutical vial.

7. The method of claim 5, further comprising:
    collecting data associated with the rejection of the dispensed pharmaceutical; and
    storing the data associated with the rejection of the dispensed pharmaceutical in data storage for future access.

8. The method of claim 1, wherein comparing the image of the dispensed pharmaceutical comprises:
    selecting from the data storage comprising image data associated with pharmaceuticals at least one visual attribute of the prescribed pharmaceutical; and
    comparing the at least one visual attribute to the image of the dispensed pharmaceutical.

9. The method of claim 1, wherein comparing the spectral data of the dispensed pharmaceutical comprises determining whether the spectral data of the dispensed pharmaceutical uniquely matches spectral data associated with the prescribed pharmaceutical, the method further comprising, responsive to a determination that the spectral data of the dispensed pharmaceutical does not uniquely match the spectral data associated with the prescribed pharmaceutical:
    selecting from the data storage comprising image data associated with pharmaceuticals at least one visual attribute of the prescribed pharmaceutical;
    comparing the at least one visual attribute to the image of the dispensed pharmaceutical; and
    automatically determining whether the image and the at least one visual attribute of the prescribed pharmaceutical confirm that the dispensed pharmaceutical uniquely matches the prescribed pharmaceutical.

10. The method of claim 1, wherein:
    comparing the image of the dispensed pharmaceutical comprises:
        selecting from the data storage comprising image data associated with pharmaceuticals at least one visual attribute of the prescribed pharmaceutical; and
        comparing the at least one visual attribute to the image of the dispensed pharmaceutical; and
    comparing the spectral data of the dispensed pharmaceutical comprises determining whether the spectral data of the dispensed pharmaceutical uniquely matches spectral data associated with the prescribed pharmaceutical, the method further comprising, responsive to a determination that the spectral data of the dispensed pharmaceutical does not uniquely match the spectral data associated with the prescribed pharmaceutical:

selecting from the data storage comprising image data associated with pharmaceuticals at least one additional visual attribute of the prescribed pharmaceutical;
comparing the at least one additional visual attribute to the image of the dispensed pharmaceutical; and
automatically determining whether the image and the at least one additional visual attribute of the prescribed pharmaceutical confirm that the dispensed pharmaceutical uniquely matches the prescribed pharmaceutical.

11. The method of claim 1, further comprising:
collecting at least one of image and spectral data associated with the dispensed pharmaceutical; and
storing the at least one of image and spectral data associated with the dispensed pharmaceutical in data storage for future access.

12. The method of claim 1, further comprising remotely updating at least one of the image data storage and the spectral data storage.

13. The method of claim 1, wherein the identifying indicia comprises a bar code.

14. A system for verification of dispensed pharmaceuticals, comprising:
an identification station configured to read identifying indicia on a pharmaceutical vial containing a dispensed pharmaceutical;
an image station configured to acquire an image of the dispensed pharmaceutical through the vial;
a spectroscopy station configured to acquire spectral data for the dispensed pharmaceutical through the vial; and
a controller associated with the identification, vision, and spectroscopy stations, wherein the controller is configured to:
receive the identifying indicia from the identification station;
automatically determine the identity of a prescribed pharmaceutical called for by the identifying indicia;
compare the identity of the prescribed pharmaceutical to data storage comprising data that indicates whether the prescribed pharmaceutical is one that can be positively distinguished by image and spectral analysis; and
responsive to the comparison of the identity of the prescribed pharmaceutical to data storage, either (a) reject the dispensed pharmaceutical when the comparison indicates that the prescribed pharmaceutical cannot be positively distinguished by image and spectral analysis, or (b) perform the following when the comparison indicates that the prescribed pharmaceutical can be positively distinguished by image and spectral analysis:
receive the image of the dispensed pharmaceutical from the image station;
compare the image of the dispensed pharmaceutical to data storage comprising image data associated with pharmaceuticals;
receive the spectral data of the dispensed pharmaceutical from the spectroscopy station;
compare the spectral data of the dispensed pharmaceutical to data storage comprising spectral data associated with pharmaceuticals; and
automatically determine whether the image and the spectral data of the dispensed pharmaceutical confirm that the dispensed pharmaceutical matches the prescribed pharmaceutical.

15. The system of claim 14, wherein the controller is configured to approve the dispensed pharmaceutical responsive to a determination that the image and the spectral data of the dispensed pharmaceutical confirm that the dispensed pharmaceutical matches the prescribed pharmaceutical.

16. The system of claim 15, wherein the controller is configured to:
collect data associated with the approval of the dispensed pharmaceutical; and
store the data associated with the approval of the dispensed pharmaceutical in data storage for future access.

17. The system of claim 14, wherein the controller is configured to reject the dispensed pharmaceutical responsive to a determination that the image and the spectral data of the dispensed pharmaceutical do not confirm that the dispensed pharmaceutical matches the prescribed pharmaceutical.

18. The system of claim 17, wherein the controller is configured to:
collect data associated with the rejection of the dispensed pharmaceutical; and
store the data associated with the rejection of the dispensed pharmaceutical in data storage for future access.

19. The system of claim 14, wherein the controller is configured to:
select from the data storage comprising image data associated with pharmaceuticals at least one visual attribute of the prescribed pharmaceutical; and
compare the at least one visual attribute with the image of the dispensed pharmaceutical.

20. The system of claim 14, wherein the controller is configured to:
collect at least one of image and spectral data associated with the dispensed pharmaceutical; and
store the at least one of image and spectral data associated with the dispensed pharmaceutical in data storage for future access.

21. The system of claim 14, wherein at least one of the image data storage and the spectral data storage is remotely updated.

22. The system of claim 14, wherein the identification station comprises a bar code scanning station, and wherein the identifying indicia comprises a bar code.

23. A computer program product for operating a dispensed pharmaceutical verification system including an identification station configured to read identifying indicia on a pharmaceutical vial containing a dispensed pharmaceutical, an image station configured to acquire an image of the dispensed pharmaceutical through the vial, and a spectroscopy station configured to acquire spectral data for the dispensed pharmaceutical through the vial, the computer program product comprising a non-transitory computer readable storage medium having computer readable program code embodied therein, the computer readable program code configured to:
receive the identifying indicia from the identification station;
automatically determine the identity of a prescribed pharmaceutical called for by the identifying indicia;
compare the identity of the prescribed pharmaceutical to data storage comprising data that indicates whether the prescribed pharmaceutical is one that can be positively distinguished by image and spectral analysis; and
responsive to the comparison of the identity of the prescribed pharmaceutical to data storage, either (a) reject the dispensed pharmaceutical when the comparison indicates that the prescribed pharmaceutical cannot be positively distinguished by image and spectral analysis, or (b) perform the following when the comparison indicates that the prescribed pharmaceutical can be positively distinguished by image and spectral analysis:
receive the image of the dispensed pharmaceutical from the image station;
compare the image of the dispensed pharmaceutical to data storage comprising image data associated with pharmaceuticals;
receive the spectral data of the dispensed pharmaceutical from the spectroscopy station;
compare the spectral data of the dispensed pharmaceutical to data storage comprising spectral data associated with pharmaceuticals; and
automatically determine whether the image and the spectral data of the dispensed pharmaceutical confirm that the dispensed pharmaceutical matches the prescribed pharmaceutical.

* * * * *

UNITED STATES PATENT AND TRADEMARK OFFICE
CERTIFICATE OF CORRECTION

PATENT NO. : 8,374,965 B2
APPLICATION NO. : 12/623822
DATED : February 12, 2013
INVENTOR(S) : Friend et al.

It is certified that error appears in the above-identified patent and that said Letters Patent is hereby corrected as shown below:

On Title Page:
Item (60) Related U.S. Application Data:
    Please add the following immediately after "Nov. 26, 2008"
        -- , and Provisional application No. 61/118,014, filed on Nov. 26, 2008 --

In the Specifications:
Column 1, Line 7, RELATED APPLICATION: Please replace the paragraph in its entirety with the following:

This application claims priority from U.S. Provisional Patent Application No. 61/118,011, filed Nov. 26, 2008, and U.S. Provisional Patent No. 61/118,014, filed Nov. 26, 2008, the disclosures of each of which is hereby incorporated by reference herein in its entirety.

Signed and Sealed this
Fourteenth Day of May, 2013

Teresa Stanek Rea
*Acting Director of the United States Patent and Trademark Office*